United States Patent [19]

Cregg

[11] Patent Number: 5,032,516

[45] Date of Patent: Jul. 16, 1991

[54] *PICHIA PASTORIS* ALCOHOL OXIDASE II REGULATORY REGION

[75] Inventor: James M. Cregg, San Diego, Calif.

[73] Assignee: Phillips Petroleum Company, Bartlesville, Okla.

[21] Appl. No.: 211,007

[22] Filed: Jun. 24, 1988

Related U.S. Application Data

[63] Continuation-in-part of Ser. No. 791,013, Oct. 25, 1985, Pat. No. 4,882,279.

[51] Int. Cl.$^5$ .................. C12N 1/16; C12P 21/02; C07H 21/04; C12R 1/84
[52] U.S. Cl. .................. 435/172.3; 435/320.1; 435/69.1; 435/255; 435/256; 536/27; 935/37
[58] Field of Search .............. 435/172.3, 320, 255, 435/256, 254; 536/27; 935/37

[56] References Cited

U.S. PATENT DOCUMENTS 4,895,800  1/1990  Tschopp et al. .................. 435/172.3

FOREIGN PATENT DOCUMENTS 0173378      3/1986  European Pat. Off. ......... 435/172.3
851137.2     4/1986  European Pat. Off. ........... 435/69.1
86114700.7   1/1987  European Pat. Off. ........... 435/64.1

OTHER PUBLICATIONS

Isolation of Alcohol Oxidase and Two Other Methanol Regulatable Genes from the Yeast *Pichia pastoris*, Molecular and Cellular Biology, vol. 5, pp. 1111-1121 (1985).

Oxidation of Methanol by the Yeast *Pichia pastoris* Purification and Properties of the Alcohol Oxidase, Agric. Biol. Chem., vol. 44, pp. 2279-2289 (1980).

*Primary Examiner*—Robin L. Teskin
*Attorney, Agent, or Firm*—Hal Brent Woodrow

[57] ABSTRACT

A novel DNA sequence derived from *Pichia pastoris* containing a regulatory region from a second alcohol oxidase gene, and novel DNA constructs comprising said regulatory region operably linked to a heterologous DNA structural gene.

4 Claims, 10 Drawing Sheets

PICHIA PASTORIS ALCOHOL OXIDASE II REGULATORY REGION

This application is a continuation-in-part of application Ser. No. 06/791,013, filed Oct. 25, 1985, now U.S. Pat. No. 4,882,279.

This invention relates to the field of recombinant DNA biotechnology. In one of its aspects the invention relates to DNA sequences which regulate the transcription of DNA. In another aspect the invention relates to vectors which incorporate the above-described DNA sequences. In yet another aspect, the invention relates to novel cells transformed with the above-described vectors.

The present invention relates generally to the manipulation of genetic material, particularly to the regulation of the frequency of transcription of RNA from DNA. This invention specifically relates to a regulatory region of the *Pichia pastoris* alcohol oxidase II gene.

BACKGROUND OF THE INVENTION

As recombinant DNA biotechnology has developed in recent years, the controlled production by cells of an enormous variety of useful polypeptides has become possible. Many eukaryotic polypeptides, for example human growth hormone, leukocyte interferons, human insulin and human proinsulin have been produced by various microorganisms. The continued application of techniques already in hand is expected in the future to permit recombinant production of a variety of other useful polypeptide products.

The basic techniques employed in the field of recombinant technology are known by those of skill in the art. The elements desirably present for the practice of recombinant DNA biotechnology include, but are not limited to:

(1) a gene encoding one or more desired polypeptide(s), operably linked (operably linked refers to a juxtaposition wherein the components are configured so as to perform their usual function) with adequate control sequences required for expression in the host cell;

(2) a vector, usually a plasmid into which a nucleotide sequence can be inserted; a vector is any nucleotide sequence-containing construct capable of transforming a host;

(3) a suitable host into which the desired nucleotide sequence can be transferred, where the host also has the cellular apparatus to allow expression of the information coded for by the transferred nucleotide sequence.

A basic element employed in recombinant technology is the plasmid, which is circular extrachromosomal double-stranded DNA first found in microorganisms. Plasmids have been found to occur in multiple copies per cell. In addition to naturally occurring plasmids, a variety of man-made plasmids have been prepared. Included in the plasmid is information required for plasmid reproduction, i.e., an autonomous replicating sequence and/or an origin of replication. One or more means of phenotypically selecting the plasmid in transformed cells may also be included in the information encoded in the plasmid. The phenotypic or marker selection characteristics, such as resistance to antibiotics, permit clones of the host cell containing the plasmid of interest to be recognized and selected for by preferential growth of the cells in selective media. Vectors or plasmids may be specifically cleaved by one or more restriction endonucleases or restriction enzymes, each of which recognizes a specific nucleotide sequence. Thereafter, a regulatory region operably linked to a heterologous gene, i.e., a gene not naturally occurring in combination with the regulatory region, or other nucleotide sequences may be inserted by operably linking the desired genetic material at the cleavage site or at reconstructed ends adjacent to the cleavage site.

The vector is then introduced into a host cell, where its nucleotide sequence may direct the host to perform various processes or functions. A few examples include expressing heterologous polypeptides or over-expressing homologous or heterologous polypeptides. The process of nucleotide introduction into the host cell is generally termed transformation. Large quantities of the vector may be obtained by introducing the vector into a suitable host to increase its copy number. A host cell commonly used to increase the copy number of the vector is *E. coli*. The vectors are then isolated from the first host and introduced into a second host cell in which the desired vector-directed activities will occur, for example the production of a polypeptide. The production of an end product from DNA in this fashion is referred to as expression. When the gene is properly inserted in the vector with reference to the portions of the vector which govern transcription and translation of the encoded nucleotide sequence, the resulting vector can be used to direct the production of the polypeptide sequence for which the inserted gene codes.

Expression is controlled by a regulatory region. Regulatory regions are heterogeneous nucleotide sequences which respond to various stimuli and affect the frequency of RNA transcription. Expression may be switched on or off in response to stimuli. Expression being switched on in response to a stimuli is commonly referred to as derepression or induction. A few examples of inducible expression systems are the AOX1 system in *Pichia pastoris*, the estrogen systems in *Xenopus laevis*, and the metallothionein systems in monkeys, humans, hamsters, mice and rats. Inducible expression systems are usually under more stringent control than constitutive systems. These systems are well suited for genetic engineering purposes.

In practice, the use of recombinant DNA biotechnology may create cells capable of expressing heterologous nucleotide sequences. Heterologous nucleotide sequences are nucleotide sequences which do not naturally occur in the host. Examples of which would be new combinations of regulatory regions naturally occurring within the host with structural genes not naturally associated with this regulatory region. Another example would be the combination of a regulatory region with a gene not naturally occurring in the host. The heterologous polypeptide may be produced as a fusion polypeptide, i.e., a heterologous polypeptide fused to a portion of the amino acid sequence of a homologous or heterologous polypeptide. The initially obtained fusion polypeptide product is sometimes produced in an inactive form until the fused polypeptide is cleaved in an extracellular environment.

As was previously disclosed in European patent application No. 86114700.7 (incorporated herein by reference) the *Pichia pastoris* genome encodes two functional alcohol oxidase genes AOX1 and AOX2.

We have now discovered a 5' regulatory region associated with the AOX2 structural gene. This regulatory region is inducible by methanol or by carbon source starvation. However, the maximum level of expression from the AOX2 regulatory region is only about 5%-11% of that of the AOX1 regulatory region (AOX1 gene was disclosed in European patent application No. 85201235.0 incorporated herein by reference).

The AOX2 regulatory region can be employed to express heterologous genes and is particularly useful in those situations where high level expression of a protein is disadvantageous.

SUMMARY OF THE INVENTION

In accordance with the present invention, we have discovered, isolated and characterized a DNA sequence which regulates the frequency of the transcription of DNA into RNA. The novel DNA sequences of this invention are useful for the production of polypeptide products by methylotrophic yeasts such as *Pichia pastoris*.

DETAILED DESCRIPTION OF THE INVENTION

In accordance with the present invention, there is provided a novel DNA sequence containing a regulatory region responsive to at least one of the following conditions: the presence of methanol in the host environment or carbon source starvation when the host cell is grown on substrates other than methanol. The regulatory region of this invention is capable of controlling the frequency of transcription of RNA when operably linked at the 5' end of a DNA sequence which codes for the production of mRNA.

In accordance with still another embodiment of the present invention, plasmids and transformed organisms containing the above-described DNA sequences and methods for producing the same are provided.

These and other objects of the invention will become apparent from the disclosure and claims herein provided.

I. Characterization of the Alcohol Oxidase Regulatory Region

Figure 1:
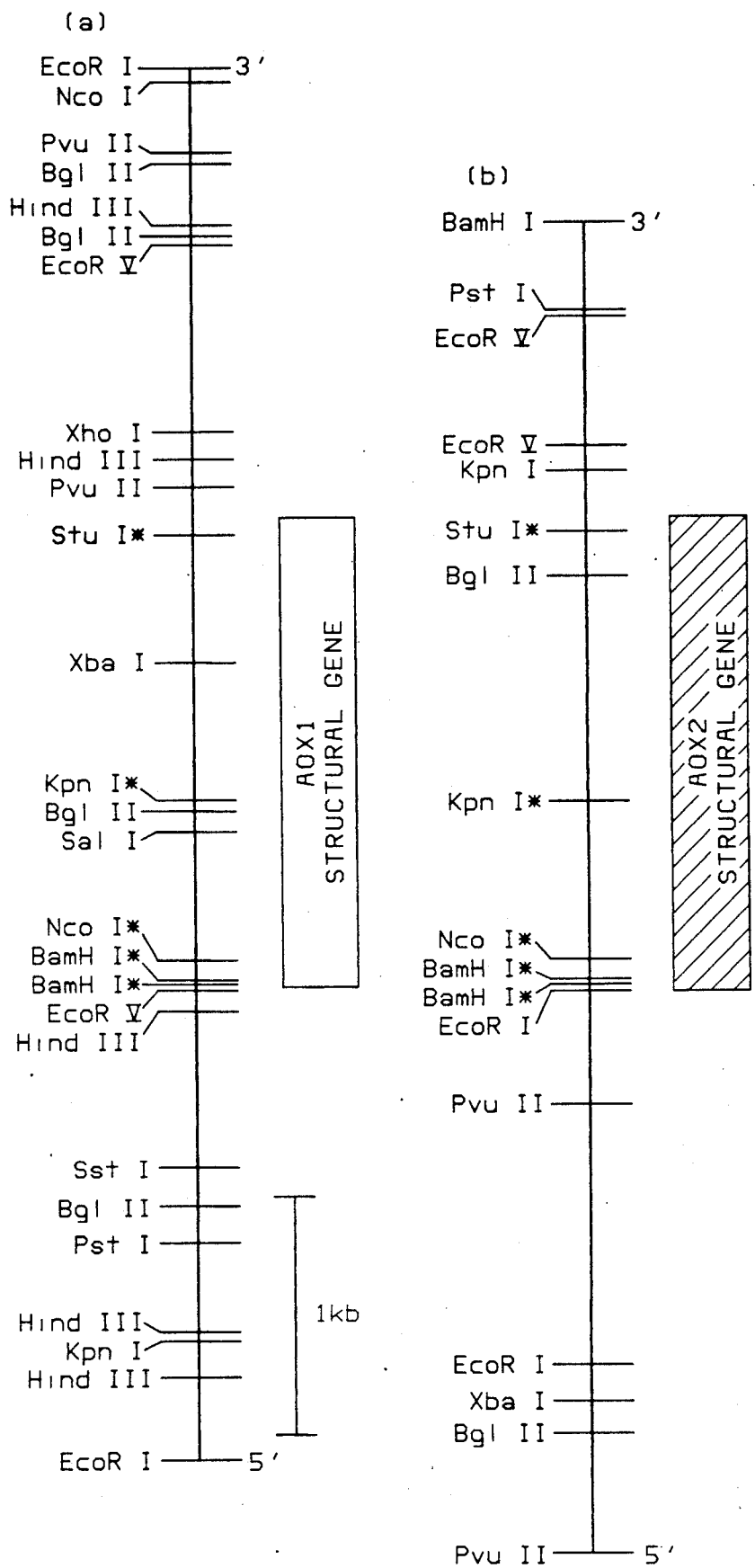
FIG. 1 provides the restriction map of the AOX1 (a) and AOX2 (b) genes.
Figure 2:
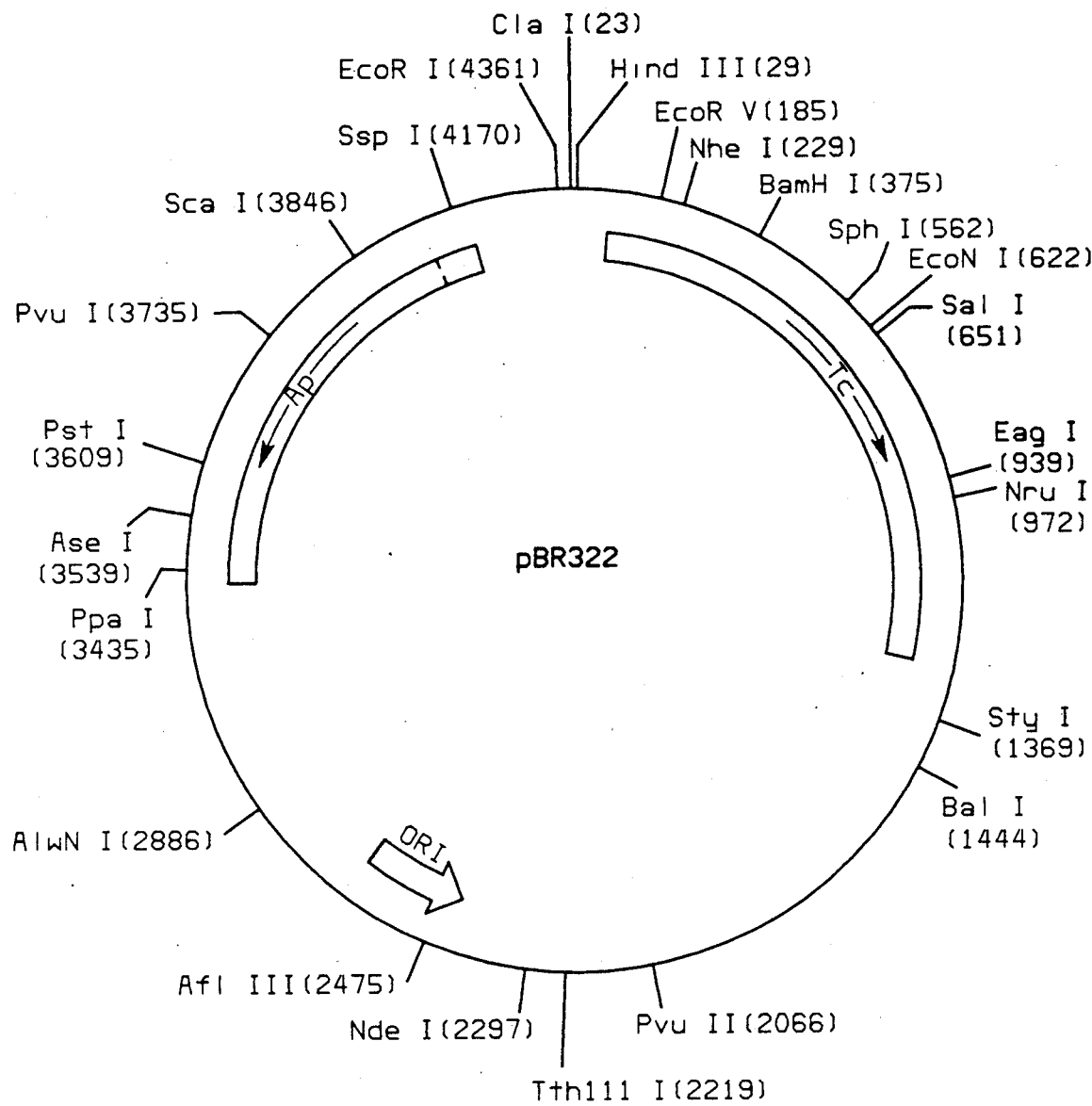
FIG. 2 provides a restriction map of the pBR322.
Figure 4:
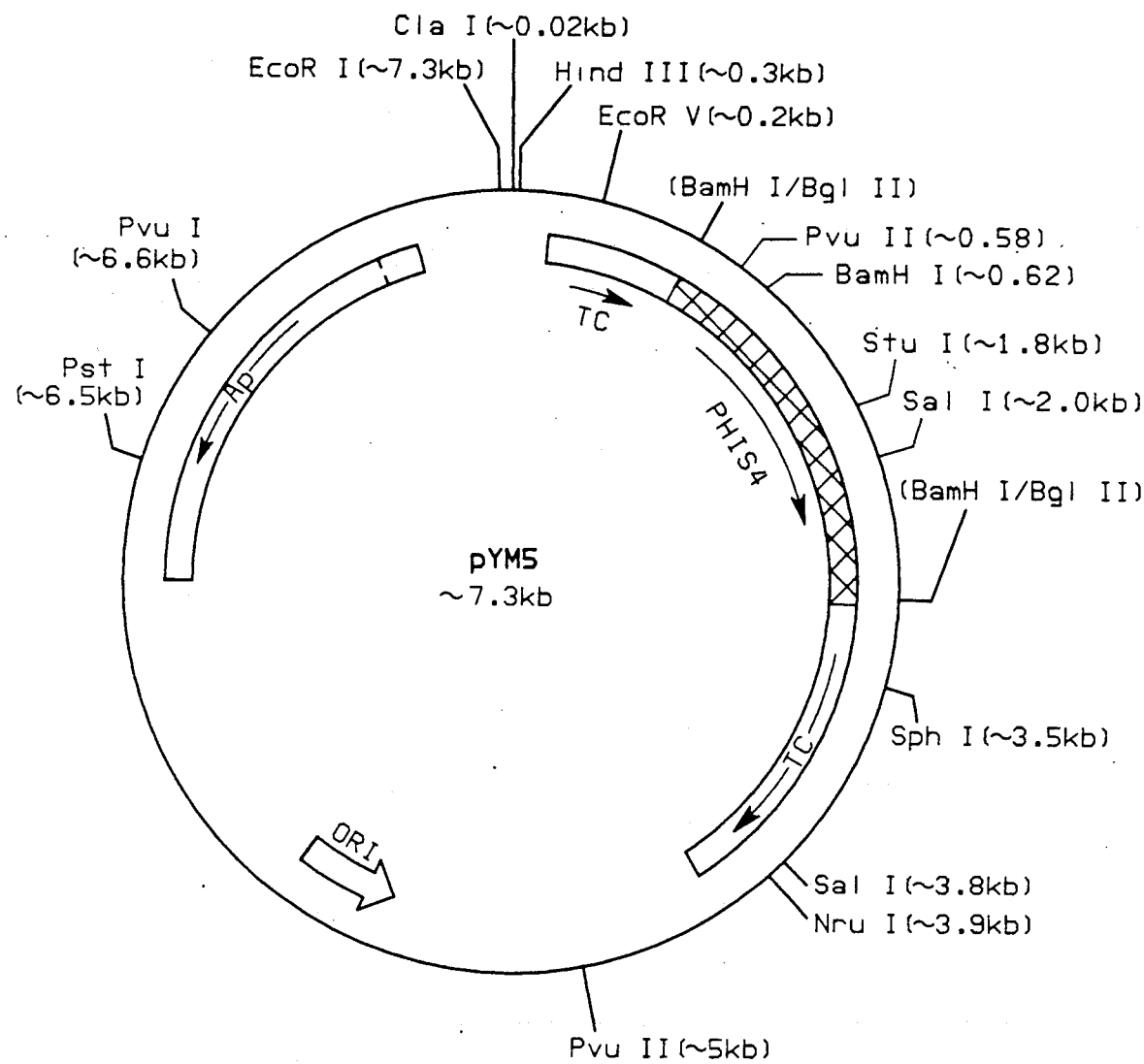
FIG. 4 provides a restriction map of plasmid pYM5.

The complete AOX2 gene is contained within the restriction map provided in FIG. 1(b). The AOX2 regulatory region is contained between the first EcoRI site from the 5' end and the start codon of the AOX2 structural gene as shown by the restriction map of FIG. 1(b). The portion of the DNA sequence encoding the alcohol oxidase II protein is indicated by the heavy bar under the restriction map. A restriction map of the alcohol oxidase I gene is provided for comparison of the two genes, FIG. 1(a). No significant sequence homology was observed outside the protein-coding portion of the genes.

The AOX2 regulatory region has been further characterized by a lacZ fusion construct, to require no more than from about base pair −1500 to about base pair −1 for regulatory activity (as shown in Table 1). The nucleotide sequence for a DNA fragment containing the AOX2 regulatory region is provided in Table 1.

TABLE 1

| A0X2 Regulatory Region and 5' Untranslated Region |
|---|
| −1750　　　　　　　−1730　　　　　　　−1710 |
| GGATCTCAAAAACCTAAGTACTTCATTTGAATATAACTCTGCACCTAAAATTTACACCTAA |
| −1690　　　　　　　−1670　　　　　　　−1650 |
| CTCTCTATCTAGGCTCTAGATTTGATAGATTCTATAGCCTTTGGTTTGTTATAGTGTTCA |
| −1630　　　　　　　−1610　　　　　　　−1590 |
| CCAACTGGATGTCCTAACGAAATGGTTCTGTGGTCTAGTTGGTTATGGCATATGCTTAAC |
| −1570　　　　　　　−1550　　　　　　　−1530 |
| ACGCATAACGTCCCCAGTTCGATCCTGGGCAGAATCATTATTTTTTGACCGAATTCTTTT |
| −1510　　　　　　　−1490　　　　　　　−1470 |
| TTTCAGACCATATGACCGGTCCATCTTCTACGGGGGGATTATCTATGCTTTGACCTCTAT |
| −1450　　　　　　　−1430　　　　　　　−1410 |
| CTTGATTCTTTTATGATTCAAATCACTTTTACGTTATTTATTACTTACTGGTTATTTACT |
| −1390　　　　　　　−1370　　　　　　　−1350 |
| TAGCGCCTTTTCTGAAAAACATTTACTAAAAATCATACATCGGCACTCTCAAACACGACA |
| −1330　　　　　　　−1310　　　　　　　−1290 |
| GATTGTGATCAAGAAGCAGAGACAATCACCACTAAGGTTGCACATTTGAGCCAGTAGGCT |
| −1270　　　　　　　−1250　　　　　　　−1230 |
| CCTAATAGAGGTTCGATACTTATTTTGATAATACGACATATTGTCTTACCTCTGAATGTG |
| −1210　　　　　　　−1190　　　　　　　−1170 |
| TCAATACTCTCTCGTTCTTCGTCTCGTCAGCTAAAAATATAACACTTCGAGTAAGATACG |
| −1150　　　　　　　−1130　　　　　　　−1110 |
| CCCAATTGAAGGCTACGAGATACCAGACTATCACTAGTAGAACTTTGACATCTGCTAAAG |

TABLE 1-continued

AOX2 Regulatory Region and 5' Untranslated Region

```
          -1090                    -1070                    -1050
CAGATCAAATATCCATTTATCCAGAATCAATTACCTTCCTTTAGCTTGTCGAAGGCATGA

-1030                    -1010                     -990
AAAAGCTACATGAAAATCCCCATCCTTGAAGTTTTGTCAGCTTAAAGGACTCCATTTCCT

-970                     -950                     -930
AAAATTTCAAGCAGTCCTCTCAACTAAATTTTTTTCCATTCCTCTGCACCCAGCCCTCTT

-910                     -890                     -870
CATCAACCGTCCAGCCTTCTCAAAAGTCCAATGTAAGTAGCCTGCAAATTCAGGTTACAA

-850                     -830                     -810
CCCCTCAATTTTCCATCCAAGGGCGATCCTTACAAAGTTAATATCGAACAGCAGAGACTA

-790                     -770                     -750
AGCGAGTCATCATCACCACCCAACGATGGTGAAAAACTTTAAGCATAGATTGATGGAGGG

-730                     -710                     -690
TGTATGGCACTTGGCGGCTGCATTAGAGTTTGAAACTATGGGGTAATACATCACATCCGG

-670                     -650                     -630
AACTGATCCGACTCCGAGATCATATGCAAAGCACGTGATGTACCCCGTAAACTGCTCGGA

-610                     -590                     -570
TTATCGTTGCAATTCATCGTCTTAAACAGTACAAGAAACTTTATTCATGGGTCATTGGAC

-550                     -530                     -510
TCTGATGAGGGGCACATTTCCCCAATGATTTTTTGGGAAAGAAAGCCGTAAGAGGACAGT

-490                     -470                     -450
TAAGCGAAAGAGACAAGACAACGAACAGCAAAAGTGACAGCTGTCAGCTACCTAGTGGAC

-430                     -410                     -390
AGTTGGGAGTTTCCAATTGGTTGGTTTTGAATTTTTACCCATGTTGAGTTGTCCTTGCTT

-370                     -350                     -330
CTCCTTGCAAACAATGCAAGTTGATAAGACATCACCTTCCAAGATAGGCTATTTTTGTCG

-310                     -290                     -270
CATAAATTTTTGTCTCGGAGTGAAAACCCCTTTTATGTGAACAGATTACAGAAGCGTCCT

-250                     -230                     -210
ACCCTTCACCGGTTGAGATGGGGAGAAAATTAAGCGATGAGGAGACGATTATTGGTATAA

-190                     -170                     -150
AAGAAGCAACCAAAATCCCTTATTGTCCTTTTCTGATCAGCATCAAAGAATATTGTCTTA

-130                     -110                      -90
AAACGGGCTTTTAACTACATTGTTCTTACACATTGCAAACCTCTTCCTTCTATTTCGGAT

-70                      -50                      -30
CAACTGTATTGACTACATTGATCTTTTTTAACGAAGTTTACGACTTACTAAATCCCCACA

-10
AACAAATCAACTGAGAAAA
```

The AOX2 regulatory region is responsive to at least one of the following conditions: the presence of methanol as the sole carbon source for methylotrophic yeast hosts, such as *Pichia pastoris*, or carbon source starvation of said host cells. Additionally the AOX2 regulatory region stimulates approximately 5%–11% of the protein production of β-galactosidase as the AOX1 regulatory region.

II. Isolation of Alcohol Oxidase II Regulatory Region from Pichia pastoris

Figure 5:
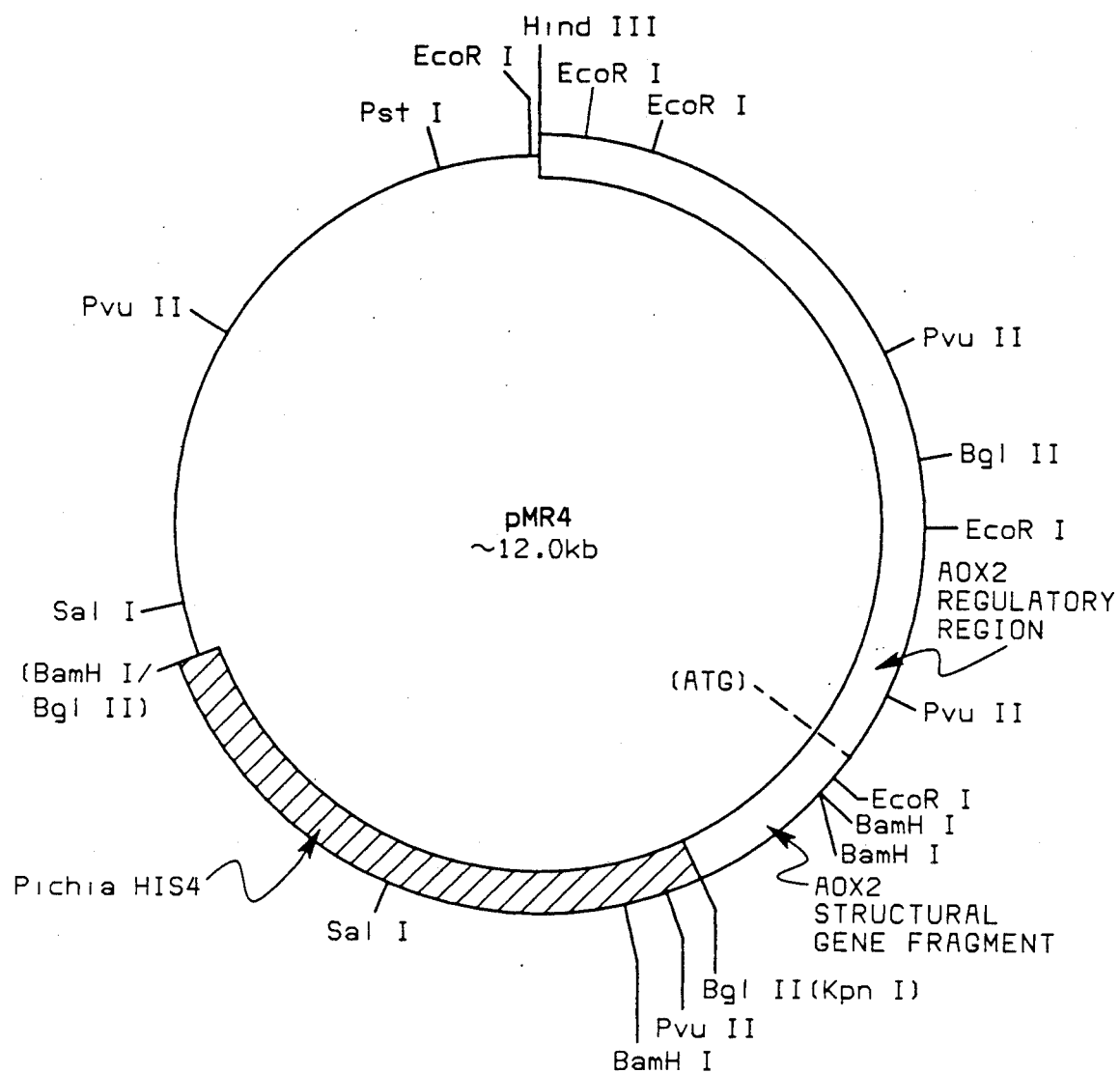
FIG. 5 provides a restriction map of plasmid pMR4.
Figure 3:
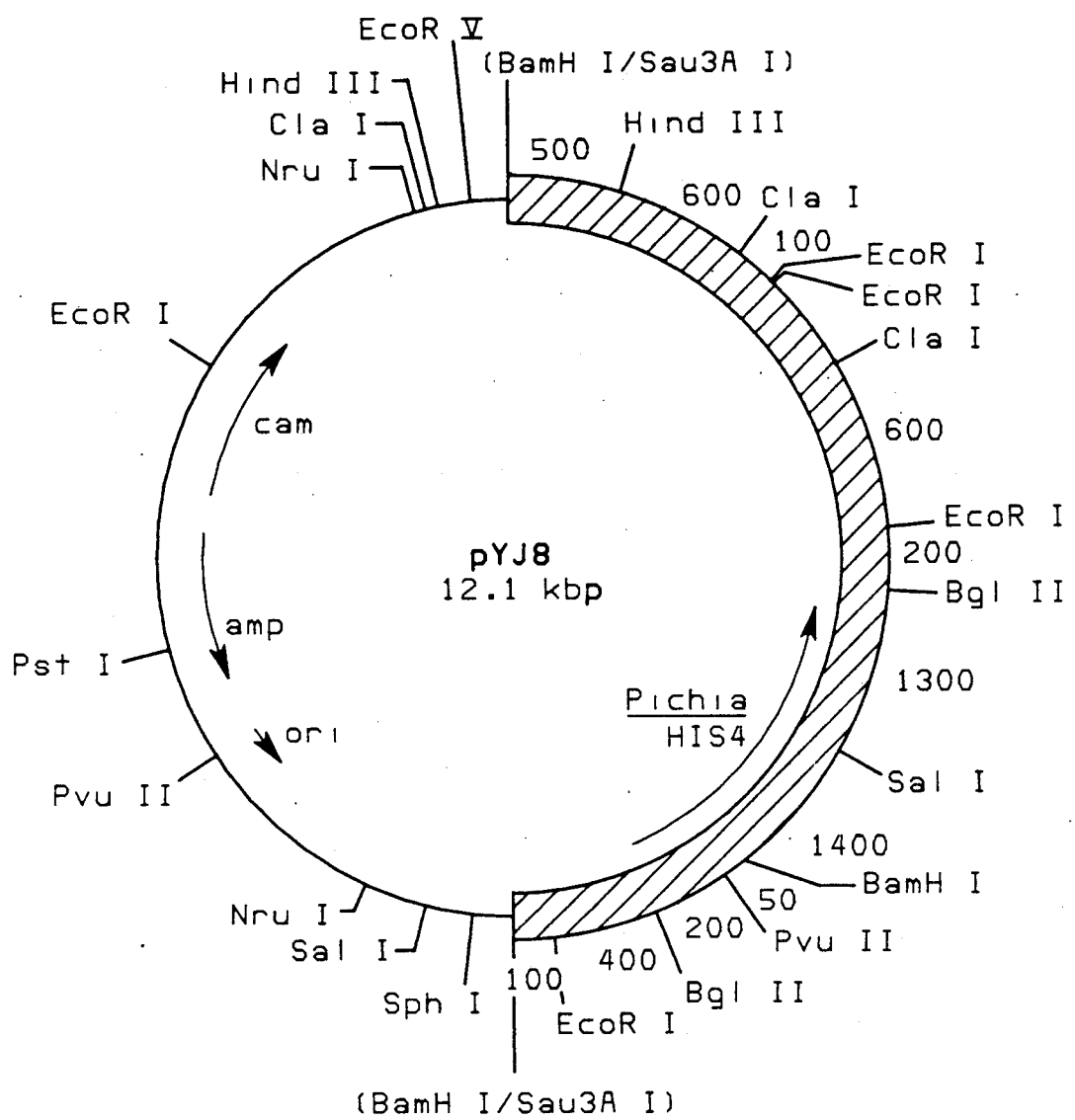
FIG. 3 provides a restriction map of pYJ8.

The AOX2 regulatory region was isolated by transforming Pichia strain MC100-3 (arg4 his4 aox1Δ::SARG4 aox2Δ::Phis4). This strain contains a mutant copy of the Pichia HIS4 gene inserted into the AOX2 gene MC100-3 was transformed with pYM5, a plasmid composed of a 2.7 kb BglII fragment containing the Pichia HIS4 gene inserted at the BamHI site of pBR322. DNAs from several MC100-3 (pYM5) His+ transformants were screened by Southern filter hybridization for transformants which contained pYM5 integrated with the HIS4 fragment located in the AOX2 locus of MC100-3. The DNA from one of these strains was then digested with HindIII, which resulted in the release of a genomic fragment of about 12 kb containing 5.3 kb of the sequence 5' of the AOX2 Kpn I site, 2.7 kb of the Pichia HIS4 gene, and 4.0 kb of pBR322. The HindIII-cut DNA was ligated and transformed into E. coli. Transformants were selected by resistance to ampicillin. A plasmid, pMR4, was recovered and a restriction map of this plasmid is shown in FIG. 5.

III. Properties of the AOX2 Regulatory Region

Figure 10:
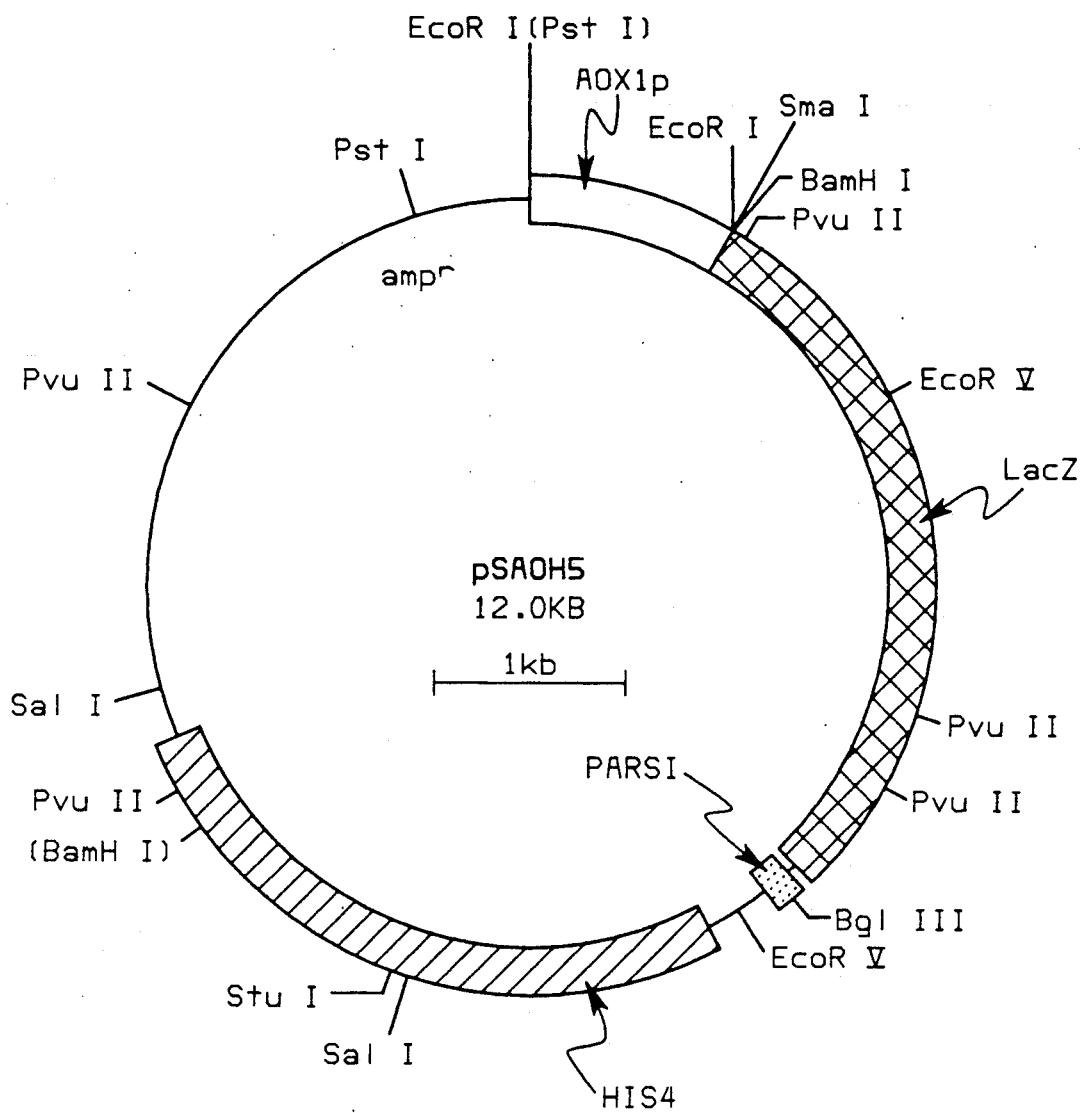
FIG. 10 provides a restriction map of plasmid pSAOH5.
Figure 6:
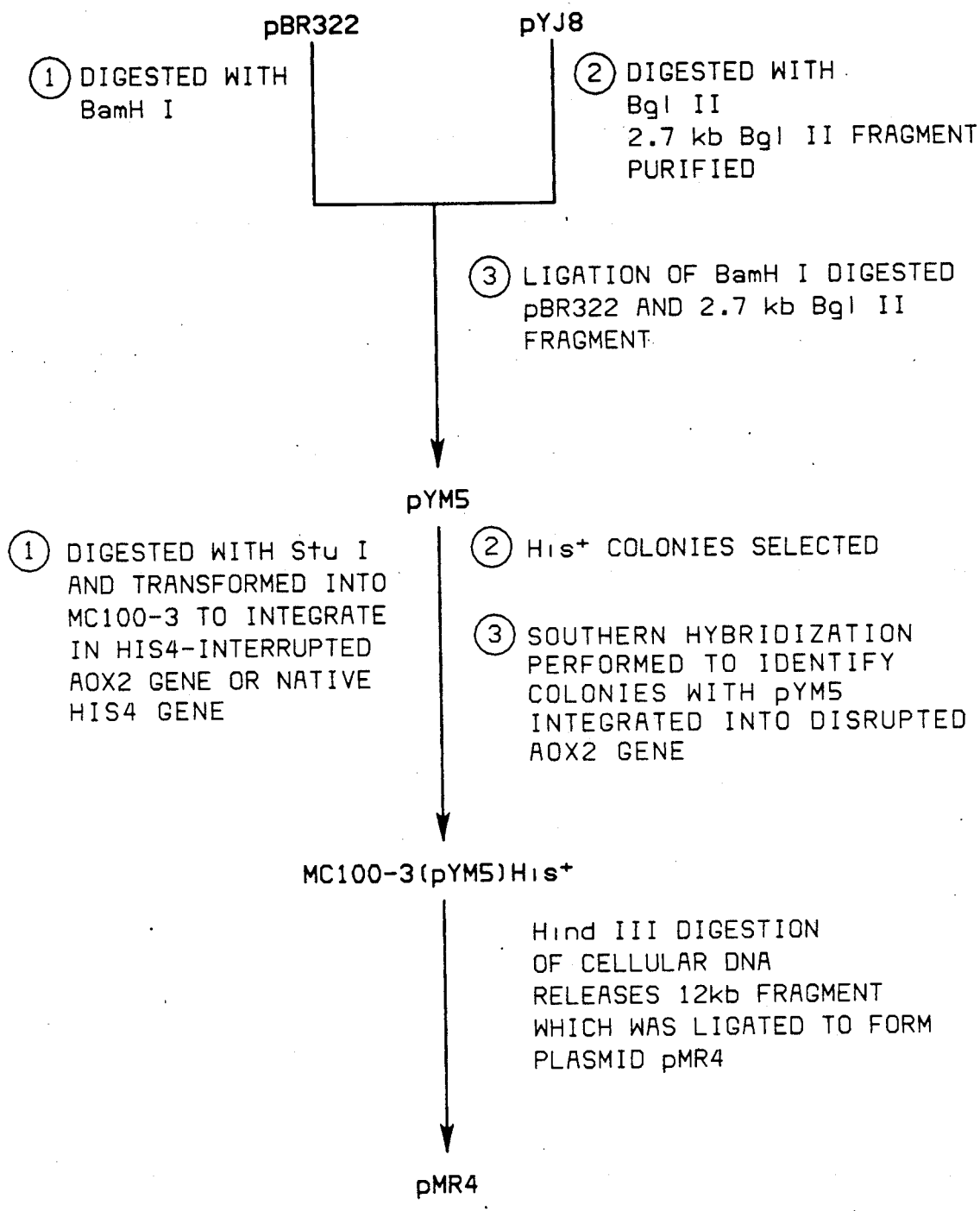
FIG. 6 provides a flow chart of the construction of pMR4.
Figure 7:
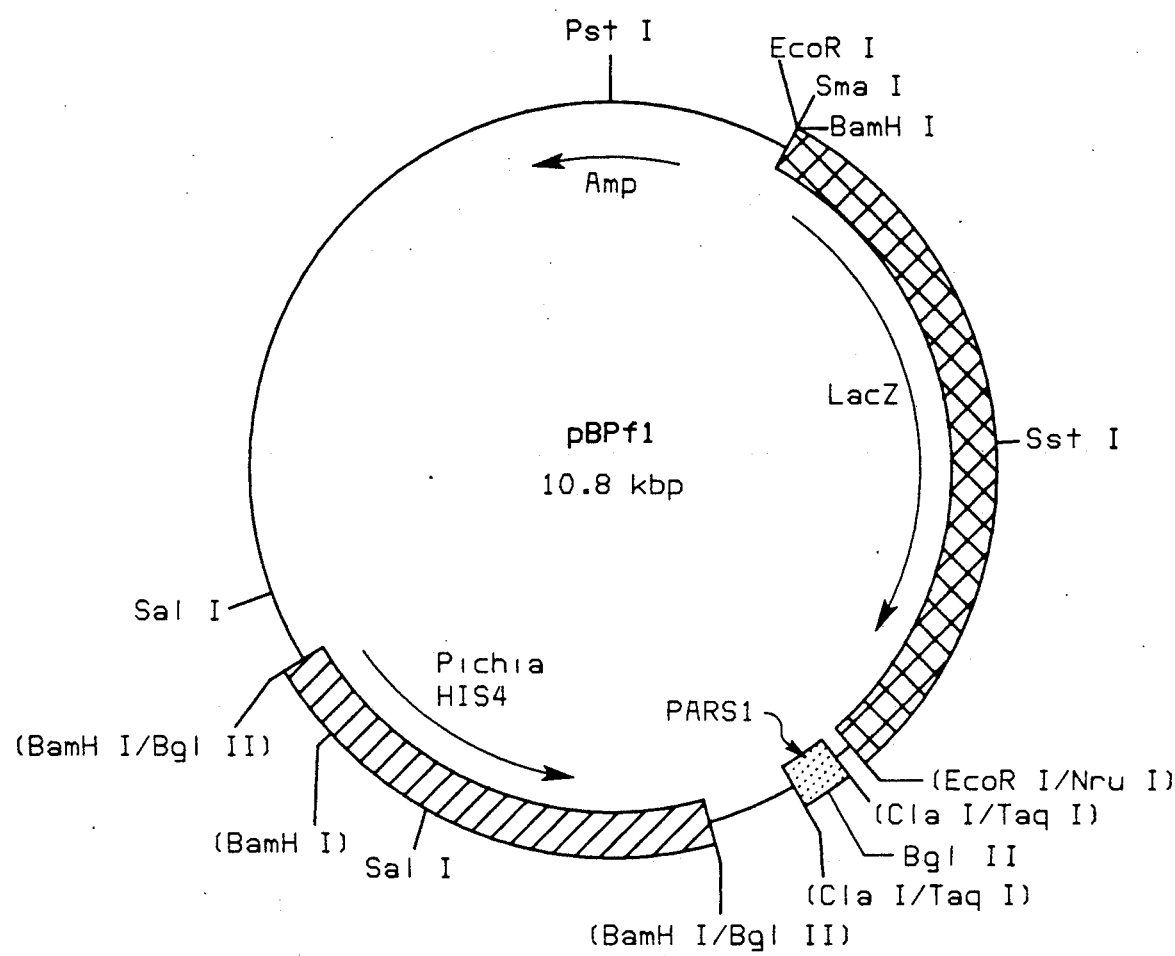
FIG. 7 provides a restriction map of plasmid pBPf1.
Figure 8:
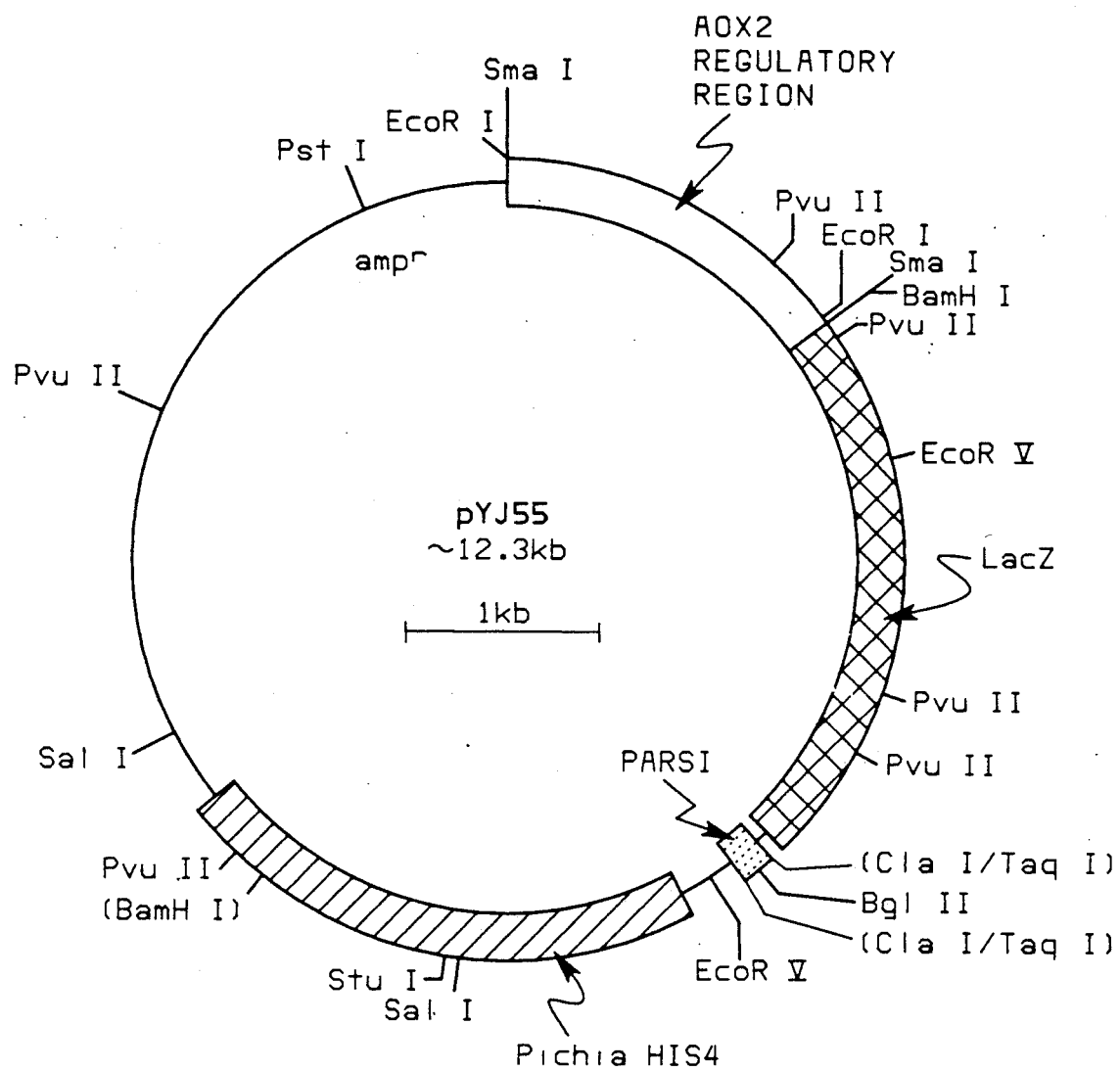
FIG. 8 provides a restriction map of plasmid pYJ55.
Figure 9:
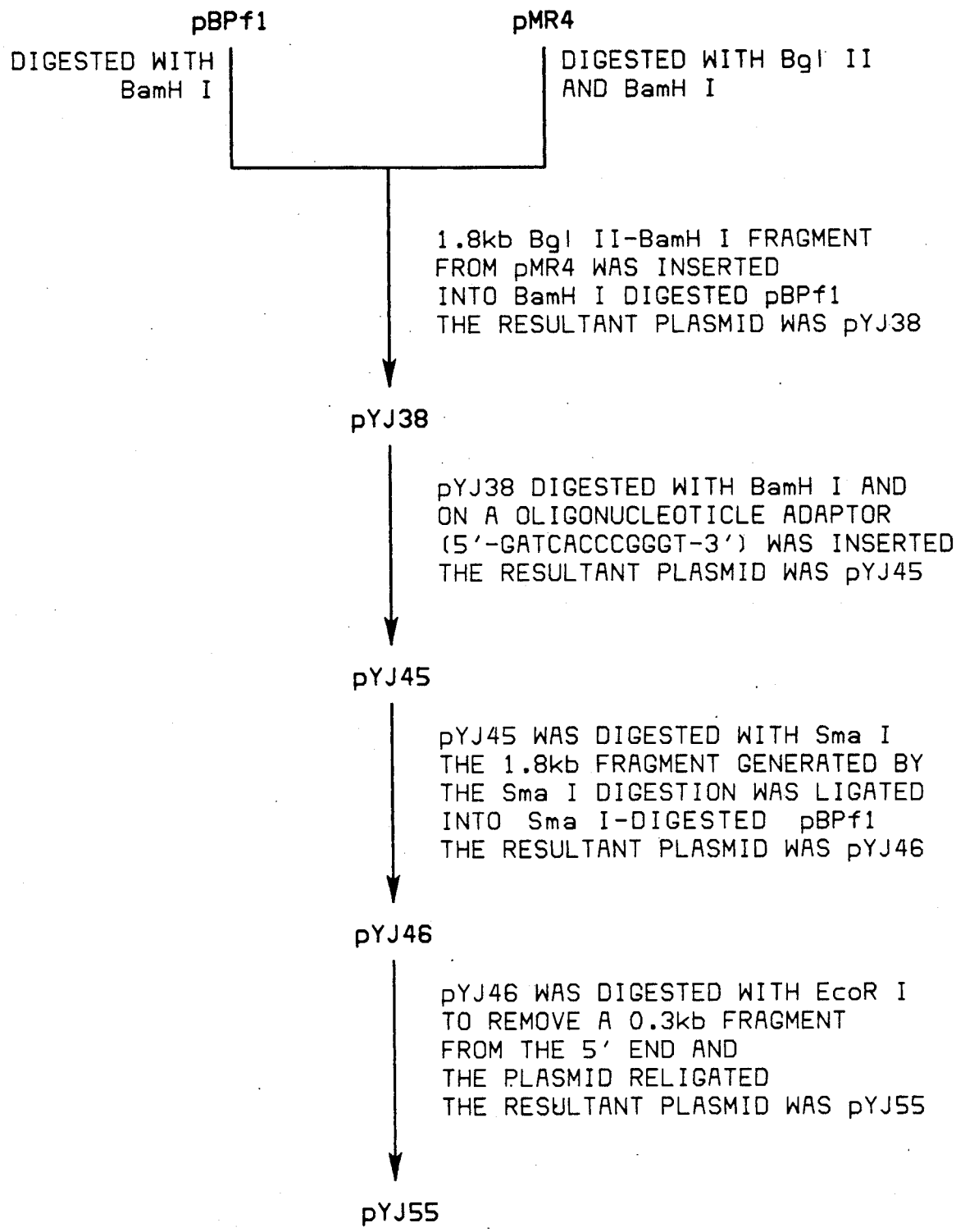
FIG. 9 provides a flow chart of the construction of plasmid pYJ55.

To compare expression of the AOX2 regulatory region to that of AOX1, an AOX2-lacZ expression vector was constructed which was as similar as possible to pSAOH5 (shown in FIG. 10), an AOX1-lacZ fusion vector. The flow chart for construction of the AOX2- lacZ vector, pYJ55, is shown in FIG. 9. Preliminary DNA sequence data from the 5' end of AOX2 revealed that AOX2 contains two BamHI sites in positions in the structural gene identical to those found in AOX1 structural gene. Therefore, the first step in the construction of pYJ55 was to insert a 1.8 kb BglII-BamHI fragment which contains the AOX2 regulatory region and 45 base pairs of the amino-terminal protein-encoding sequence, into the BamHI site of pBPf1 to create pYJ38. The second step was to cut pYJ38 with BamHI and insert the same adaptor oligonucleotide which was inserted for the construction of the AOX1-lacZ vector (5'-GATCACCCGGGT-3'). The insertion of this adaptor destroyed the BamHI site of pYJ38 and created a new SmaI site at the point of insertion. This plasmid, pYJ45, was digested with SmaI, and the 1.8 kb SmaI fragment containing the modified AOX2 promoter was inserted into pBPf1 to create plasmid pYJ46. Plasmid pJY46 was digested with EcoRI to remove a 0.3 kb fragment from the 5' end of the AOX2 fragment in pYJ46. The plasmid was religated to create plasmid pYJ55. A restriction map of plasmid pYJ55 is provided in FIG. 8.

Plasmid pYJ55 was transformed into GS115 (his4), and His+ transformants were screened for a stable His+ phenotype, indicating the presence of an integrated plasmid. Genomic DNAs from several stable His+ strains were analyzed by Southern filter hybridization to confirm the presence and determine the location of the plasmid.

To estimate the relative strengths of the AOX1 and AOX2 promoters, β-galactosidase production by pYJ55 and pSAOH5 was compared by transforming these plasmids into GS115. The transformed GS115 strains were designated GS115(pYJ55) and GS115(pSAOH5) respectively. Each strain contains plasmid integrated at the HIS4 locus. Cells of each strain were grown in glycerol medium, shifted to a medium without carbon source for 24 hours, and then shifted to a medium with methanol for a further 50 hours. Samples of each culture were removed at the end of each growth phase, and extracts were prepared and assayed for β-galactosidase. The results of these assays are shown in Table 2.

TABLE 2

Comparison of β-Galactosidase Expression from AOX1- and AOX2-lacZ Fusions

| Strain | Promoter | β-Galactosidase Activity (U/μg) in Carbon Source | | |
|---|---|---|---|---|
| | | Glycerol | No Carbon[1] | Methanol[1] |
| GS115(pSAOH5) | AOX1 | <10 | 955 | 6,205 |
| GS115(pYJ55) | AOX2 | <10 | 109 | 739 |

[1] YNB medium

Significant levels of β-galactosidase were not seen in glycerol-grown cells of either the AOX1-lacZ or AOX2-lacZ strains. In the medium with no carbon source, the level of activity in the AOX2-lacZ strains was approximately one-tenth of that observed in the AOX1-lacZ strain. The addition of methanol to the AOX2-lacZ-containing cells resulted in levels of β-galactosidase which reached about one ninth of those of the AOX1-lacZ cells. Thus, the AOX1 and AOX2 genes are regulated in a similar manner. The one distinguishing feature is a significantly lower response to methanol and carbon source starvation by the AOX2 regulatory region.

Although the introduction of the AOX2 regulatory region-β-galactosidase gene fusion into a host yeast cell was described herein, those skilled in the art recognize it is not necessary for the practice of this invention to utilize circular plasmids or the β-galactosidase structural gene. Thus, other vectors capable of being maintained in yeasts can be employed in the utilization of this regulatory region with other heterologous genes. Alternatively, this regulatory region operably linked to other heterologous genes can be integrated into the chromosome of the host yeast cell using integrative vectors. Additionally, functional mutants of the AOX2 regulatory region described herein, consisting of shorter DNA sequence from the 5' end, can also be used to regulate heterologous gene expression.

EXAMPLES

General information pertinent to the Examples

| Strains | |
|---|---|
| Pichia pastoris | NRRL Y-11430 |
| Pichia pastoris | GS115 (his4) NRRL Y-15851 |
| Pichia pastoris | PPF1 (arg4 his4) NRRL Y-18017 |
| Pichia pastoris | KM7121 (agr4 his4 aox1Δ::SARG4 aox1Δ::PH1S4) NRRL Y-18019 |
| E. coli MC1061 | [F⁻araD139 Δ(ara ABD1C-leu) 7679ΔlacX74 galU galK rpsL hsdR] |

| Media, Buffers, and Solutions | |
|---|---|
| 1M Tris buffer | 121.1 g Tris base in 800 mL of H₂O; adjust pH to the desired value by adding concentrated (35%) aqueous HCl; allow solution to cool to room temperature before final pH adjustment, dilute to a final volume of 1 L. |
| TE buffer | 1.0 mM EDTA in 0.01 M (pH 7.4) Tris buffer |
| SSC | 0.15 M NaCl 15 mM sodium citrate adjusted to pH 7.0 with NaOH |
| TAE | 40 mM acetic acid 5 mM EDTA in 0.02 M (pH 8.3) Tris buffer |
| Denhardt's solution (50 ×) | 5 g Ficoll 5 g polyvinylpyrrolidone 5 g bovine serum albumin (BSA; Pentax Fraction V) brought to a total volume to 500 mL with water |
| 20 × SSPE | 20 mM EDTA 0.16 M NaOH 0.2 M NaH₂PO₄·H₂O 3.6 M NaCl adjusted to pH 7.0 with NaOH |
| LB (Luria-Bertani) medium | 5 g Bacto-tryptone 5 g Bacto-yeast extract 2.5 g NaCl in 1 L of water, adjusted to pH 7.5 with NaOH |
| YPD medium | 1% Bacto-yeast extract 2% Bacto-peptone 2% Dextrose |
| YNB medium | 6.75 g yeast nitrogen base without amino acids (DIFCO) in 1 L of water |
| SED | 1 M sorbitol 25 mM EDTA 50 mM DTT |
| SCE buffer | 9.1 g sorbitol 1.47 g sodium citrate 0.168 g EDTA 50 mL H₂O |

| Media, Buffers, and Solutions | |
|---|---|
| | pH to 5.8 with HCl |
| CaS | 1 M sorbitol |
| | 10 mM CaCl$_2$ |
| | filter sterilize |
| PEG solution | 20% polyethylene glycol-3350 |
| | 10 mM CaCl$_2$ |
| | 10 mM Tris.HCl (pH 7.4) |
| | filter sterilize |
| SOS | 1 M sorbitol |
| | 0.3 × YPD medium |
| | 10 mM CaCl$_2$ |
| Formamide dye mix | 0.1% xylene cylenol FF |
| | 0.2% bromophenol blue |
| | 10 mM EDTA |
| | 95% deionized formamide |
| Top gel | 76.8 g urea |
| | 24 mL acrylamide stock |
| | 8 mL 10 × TBE |
| | bring to final volume of 160 mL |
| Acrylamide stock | 38 g acrylamide |
| | 2 g bis(N,N-methylenebisacrylamide) |
| | add water to total volume of 100 mL |
| Bottom gel | 14.4 g urea |
| | 3.0 g sucrose |
| | 7.5 mL 10 × TBE |
| | 4.5 mL acrylamide stock |
| | 0.3 mL bromphenol blue solution |
| | (0.01 g/mL) |
| | add water to give total volume of 30 mL |
| dideoxy: | |
| dd ATP | 0.125 mM |
| dd CTP | 0.10 mM |
| dd GTP | 0.10 mM |
| dd TTP | 0.80 mM |
| DNTP stocks | 0.5 mM dGTP |
| | 0.5 mM dCTP |
| | 0.5 mM TTP |
| | 0.5 mM dATP |
| 10 × Klenow | 70 mM Tris.HCl, pH 7.5 |
| Dilution Buffer | 200 mM NaCl |
| | 70 mM MgCl$_2$ |
| | 1 mM EDTA |
| 10 × TMD, pH 7.5 | 0.1 M Tris.HCl, pH 7.5 |
| | 0.05 M MgCl$_2$ |
| | 0.075 M DTT |

Unless otherwise specified, the above solutions represent the basic (1×) concentration employed. Throughout the examples, where different concentration levels are employed, that fact is indicated by referring to the solution as a multiple of the basic (1×) concentration.

REGENERATION AGAR (1) Agar-KCl: 9 g Bacto-agar, 13.4 g potassium chloride, 240 mL H$_2$O, autoclave.

(2) 10×glucose: 20 g dextrose, 100 mL H$_2$O, autoclave.

(3) 10×YNB: 6.75 g Yeast Nitrogen Base without amino acids, 100 mL H$_2$O, autoclave. (Add any desired amino acid or nucleic acid up to a concentration of 200 μg/mL before or after autoclaving.)

(4) Add 30 mL of 10×glucose and 30 mL of 10×YNB to 240 mL of the melted Agar-KCl solution. Add 0.6 mL of 0.2 mg/mL biotin and any other desired amino acid or nucleic acid to a concentration of 20 μg/mL. Hold melted Regeneration Agar at 55°–60° C.

GROWTH OF *PICHIA PASTORIS*

*P. pastoris* was grown in YPD (rich) or YNB (minimal) medium. As required, YNB medium was supplemented with carbon source (2% dextrose, 1% glycerol, or 0.5% methanol) and with 50 μg/ml of amino acid.

SEQUENCING

DNA sequencing was by the dideoxynucleotide chain-termination method of Sanger et al., PNAS 74, 5463 (1977).

The following abbreviations are used throughout the Examples:

| EDTA | ethylenediamine tetraacetic acid |
|---|---|
| TEMED | N,N,N',N'-tetramethylenediamine |
| DTT | dithiothreitol |
| BSA | bovine serum albumin |
| EtBr | ethidium bromide |
| Ci | Curie |
| dATP | deoxyadenosine triphosphate |
| dGTP | deoxyguanosine triphosphate |
| TTP | thymidine triphosphate |
| dCTP | deoxycytidine triphosphate |
| dXTP | "generic" deoxy triphosphate nucleotide |
| oligo(dT)12_18 | Source: Collaborative Research, Inc. |
| Zymolyase 60,000 | Source: Miles Laboratories |

Isolation of the Alcohol Oxidase II Regulatory Region

EXAMPLE I

Mating of PPF1 × KM7121 and Development of MC100-3

*Pichia pastoris* PPF1 (arg4 his4) (NRRL Y-18017) and KM7121 (arg4 his4 aox1Δ::SARG4 aox2Δ::PHIS4 (NRRL Y-18019) were each inoculated from a fresh YPD plate into a tube of sterile water. About 5×10$^7$ cells of each strain were mixed, sonicated briefly to break up cell clumps, and spread on a GNAP agar plate (5% dextrose, 2% peptone, 1% yeast extract, 0.5% agar, 2.3% nutrient agar). An unmixed control sample of each strain (approximately 1×10$^8$ cells) was treated in the same manner. The GNAP plates were incubated at 30° C. for about 24 hours and then replica-plated onto sporulation medium agar plates (0.5% Na acetate, 1% KCl, 2% agar). These plates were incubated for about 20 hours at 30° C. and then replica-plated onto minimal medium agar plates with no carbon source. Methanol was fed to the cells on the minimal plates in the vapor phase.

After 5 days, about 200 colonies appeared on the minimal plate which received the mixed cells. No colonies ever developed on the unmixed control plates, a result which suggests that the Arg+ His+ Mut+ colonies on the mixed plate were diploid resulting from matings of PPF1 and KM7121 cells (Mut+ =methanol utilization) The diploid nature of these Arg+ His+ Mut+ strains was confirmed by examining the AOX loci of four of these strains by Souther filter hybridization. Specific probes utilized were: pPG3.0 (NRRL B-18022), an AOX2 specific probe; pYJ30 (NRRL B-15890), a HIS4 specific probe; and pPG4.0 (NRRL B-15868), an AOX1 specific probe.

To sporulate the PPF1 × KM7121 dipolids, a colony (MC100) was first recovered from the methanol medium diploid selection plate. About 1×10$^6$ of these cells were spread on GNAP plates and treated as described for the mating procedure, except that the sporulation plate was incubated for four days at 30° C. to allow the cells to complete sporulation. Spores were recovered from the plates by rinsing each plate with 5 ml of sterile water. The suspension was washed twice with 3 ml of phosphate buffer.(0.1M Na$_3$PO$_4$, pH 7.5). A mixture of the yeast lytic enzymes Glusulase (Endo Laboratories, NY) and Zymolyase (60,000 units/g; Miles Laboratories) and β-mercaptoethanol was added to final concentrations of 2% (v/v), 0.5 mg/ml, and 0.1%, respectively, to destroy vegetative cells. The mixture was incubated for 5 hours at 30° C.

The spore preparation was then washed twice in sterile water containing 0.2% Tween 80 (v/v) and resuspended in phosphate buffer. The preparation was then treated to three 20-second cycles of sonication to break up clumps of spores. A sample of the spore preparation was then diluted and spread on non-selective master plates of minimal medium with 2.0% glucose and 50 μg/ml each of arginine and histidine. These were incubated for 48 hours at 30° C. Each master plate was then replica-plated onto the following series of minimal plates: (1) glucose, −arg, −his (2) glucose, −arg, +his (3) glucose, +arg, −his and (4) glucose, +arg, +his.

After incubation for 24 hours at 30° C., the colonies were examined for Arg and His phenotypes. Colonies which were Arg+ His− were then tested for growth on methanol by streaking onto YNB methanol agar plates. After about one week at room temperature the plates were examined for Mut phenotype. One Arg+ His− Mut− strain was designated MC100-3.

EXAMPLE II

Transformation of Pichia pastoris

Yeast cells were inoculated into about 10 ml of YPD medium and shake cultured at 30° C. for 12-20 hours. The cells were then diluted to an $A_{600}$ of about 0.01 to 0.1 and maintained in log phase in YPD medium at 30° C. for about 6-8 hours. 100 ml of YPD medium was inoculated with 0.5 ml of the seed culture at an $A_{600}$ of about 0.1 and shake cultured at 30° C. for about 12-20 hours. The culture was then harvested when $A_{600}$ was about 0.2 to 0.3 (after approximately 16-20 hours) by centrifugation using a DAMON IEC DPR-6000 centrifuge at 1500 g for 5 minutes.

To prepare spheroplasts, the cells were washed once in 10 ml of sterile water (centrifugation was performed after each wash as described above), once in 10 ml of freshly prepared SED, once in 10 ml of sterile 1M sorbitol, and resuspended in 5 ml of SCE buffer. 5 μl of 4 mg/ml Zymolyase 60,000 (Miles Laboratories) was added and the cells incubated at 30° C. for about 30 minutes.

Spheroplast formation was monitored as follows. 100 μl aliquots of cells were added to 900 μl of 5% SDS and 900 μl of 1M sorbitol before or just after the addition of Zymolayse, and at various times during the incubation period. The incubation was stopped at the point where cells would lyse in SDS but not sorbitol. Once formed, spheroplasts were washed once in 10 ml of sterile 1M sorbitol by centrifugation at 1,000 g for 5-10 minutes, washed once in 10 ml of sterile CaS by centrifugation, and resuspended in 0.6 ml of CaS.

For the actual transformation, DNA samples in water or TE buffer were added (up to 20 μl total volume) to 12×75 mm sterile polypropylene tubes. (For small amounts of DNA, maximum transformation occurs using about 1 μl of 5 mg/ml sonicated E. coli DNA in each sample). 100 μl of spheroplasts were added to each DNA sample and incubated at room temperature for about 20 minutes. 1 ml of PEG solution was added to each sample and incubated at room temperature for about 15 minutes. The samples were centrifuged at 1,000 g for 5-10 minutes and the supernatant was discarded. The pellets were resuspended in 150 μl of SOS and incubated at room temperature for 30 minutes. 850 μl of sterile 1M sorbitol was added to each, and the samples were plated as described below.

10 ml of Regeneration Agar was poured per plate at least 30 minutes before transformation samples were ready. 10 ml aliquots of Regeneration Agar were also distributed to tubes in a 45°-50° C. bath during the period that transformation samples were in SOS. Samples were then added to the tubes, poured onto plates containing the solid bottom agar layer, and incubated at 30° C. for 3-5 days.

Spheroplast quality at various points was determined as follows. 10 μl of sample was removed and diluted 100× by addition to 990 μl of 1M sorbitol. 10 μl of the dilution was removed, and an additional 990 μl aliquot of 1M sorbitol was added. 100 μl of both dilutions were spread-plated on YPD agar medium to determine the concentration of unspheroplasted whole cells remaining in the preparation. 100 μl of each dilution was added to 10 ml of Regeneration Agar which had been supplemented with 40 μg/ml of all amino acids required by the host to determine the total regeneratable spheroplasts. Good values for a transformation experiment were $1-3\times10^7$ total regenerable spheroplasts/ml and about $1\times10^3$ whole cells/ml.

EXAMPLE III

Construction of MC100-3 (pYM5)

About 10 μg of pBR322 was digested with BamHI and dephosphorylated. About 50 μg of pYJ8 (NRRL B-15889), which contains the Pichia HIS4 gene, was digested with BglII. A 2.7 Kb BglII fragment was isolated from a 0.8% preparative agarose gel. 300 ng of the fragment and 300 ng of BamHI-digested pBR322 were ligated using 0.5 units of T4 DNA ligase in 10 μl total volume of 66 mM Tris.Cl, pH 7.4, 6.6 mM $MgCl_2$, 10 mM DTT, and 0.4 mM ATP, for 24 hours at 4° C.

The ligation reaction was used to transform E. coli MC1061 to ampicillin resistance as described in Example V. Transformants were characterized by restriction digestions, and the correct insert size and orientation was verified by agarose gel electrophoresis. This plasmid was called pYM5, and was recovered from E. coli using the alkaline lysis plasmid preparation technique described in Maniatis et al (1982) (Maniatis, T., Fritsch, E. F., and Sambrook, J. (1982). *Molecular Cloning: A Laboratory Manual*. Cold Spring Harbor Laboratory, Cold Spring Harbor, N.Y.).

About 10 μg of pYM5 was digested with StuI prior to transformation of MC100-3. This step directed the plasmid to integrate at one of the HIS4 gene sequences present in MC100-3, either the native HIS4 locus or the modified AOX2 locus. Transformation was conducted according to procedures outlined in Example II.

DNAs from several MC100-3 (pYM5) His+ transformants were isolated according to Example IV and screened by Southern filter hybridization for transformants which contained pYM5 integrated at the HIS4 fragment located at AOX2. Specific probes utilized were: pPG 3.0 (NRRL B-18022), an AOX2 specific probe; pYJ30 (NRRL B-15890), a HIS4 specific probe.

PROPERTIES OF THE ALCOHOL OXIDASE II REGULATORY REGION

EXAMPLE IV

Yeast DNA Preparation

Yeast cells were grown in 100 ml of YNB medium plus 2% dextrose at 30° C. until $A_{600}$ equaled 1-2 and then pelleted using a Damon IEC DPR-6000 centrifuge at 2,000 g for 5 minutes. The pellet was washed once in $dH_2O$, once in SED, once in 1M sorbitol and then resuspended in 5 ml of a solution of 0.1M tris.Cl, pH 7.0, and 1M sorbitol. The cells were then mixed with 50–100 μl of a 4 mg/ml solution of Zymolyase 60,000 (Miles Laboratories) and incubated at 30° C. for 1 hour. The resulting spheroplasts were then centrifuged at 1,000 g for 5–10 minutes and suspended in 5 ml Lysis Buffer [0.1% SDS, 10 mM Tris.Cl (pH 7.4), 5 mM EDTA and 50 mM NaCl]. Proteinase K (Boehringer Mannheim) and RNase A (Sigma) were each added to 100 μg/ml and the solution incubated at 37° C. for 30 minutes. DNA was deproteinized by gently mixing the preparation with an equal volume of chloroform containing isoamyl alcohol (24:1, v/v), and the phases were separated by centrifugation at 12,000 g for 20 minutes. The upper (aqueous) phase was drawn off into a fresh tube and extracted with an equal volume of phenol/chloroform/isoamyl alcohol. The phases were separated as before and the top phase placed in a tube containing 2–3 volumes of cold 100% ethanol. The sample was gently mixed and DNA was collected by spooling onto a plastic rod. The DNA was immediately dissolved in 1 mL of TE buffer and dialyzed overnight at 4° C. against 100 volumes TE buffer.

EXAMPLE V

Construction of pMR4

DNA was isolated according to the method of Example IV from a MC100-3 (pYM5) His+ transformant generated in Example III. 10 μg of this genomic DNA was digested with HindIII and ligated. The ligation reaction was carried out at 4° C. for 24 hours in 66 mM Tris.Cl, pH 7.4 6.6 mM $MgCl_2$, 10 mM DTT, 0.4 mM ATP, and 0.5 units of T4 DNA ligase.

The ligation mix was transformed directly into E. coli MC1061 cells, which had been made competent for transformation and transformed as described by Maniatis et al. (1982). Selection for ampicillin resistance was performed by culturing the cells in either LB medium or 2B medium (0.2% $NH_4PO_4$, 1.2% $Na_2HPO_4$, 0.013% $MgSO_4 \cdot 7H_2O$, 0.074% $CaCl_2 \cdot 2H_2O$, 1 μg/ml thiamine, 0.4% dextrose) supplemented with 50 μg/ml ampicillin.

A 12.0 Kb plasmid designated pMR4 was recovered according to Maniatis et al. (1982). This plasmid contained 5.3 Kb of DNA 5' of the AOX2 KpnI site, 2.7 Kb of the Pichia HIS4 gene and 4.0 Kb of pBR322.

EXAMPLE VI

Construction of pYJ55

In order to determine the regulation and expression of the AOX2 promoter, a vector containing the AOX2 5' sequence fused to the E. coli lacZ gene was constructed. 50 μg of pMR4 (Example V) was digested with BglII and BamHI according to the manufacturer's directions. A 1.8 Kb BglII-BamHI fragment containing the AOX2 promoter was isolated from a 0.8% preparative agarose gel. 10 μg of pBPfl (NRRL B-15892) was digested with BamHI and dephosphorylated using alkaline phosphatase in a 50 μl reaction volume (1 U enzyme at 37° C. for 1 hour in 50 mM Tris.Cl, pH 9.0, 1 mM $MgCl_2$, 100 μM $ZnCl_2$, 1 mM spermidine).

300 ng of the 1.8 Kb fragment and 300 ng of pBPfl were ligated with T4 ligase as follows. The ligation reaction was performed at 23° C. for 1 hour in a 10 μl reaction volume containing 66 mM Tris.Cl, pH 7.6, 5 mM $MgCl_2$, 5 mM dithiothrietol, 1 mM ATP and 1 Weiss unit of T4 ligase. The resulting vector was designated pYJ38.

A new SmaI restriction site was created in pYJ38 as follows. An adaptor oligonucleotide was synthesized using an Applied Biosystems DNA Synthesizer, Model 380 A, using cyanoethylphosphoramidite chemistry:

5'-GATCACCCGGGT-3'

10 μg of pYJ38 was digested with BamHI and treated with alkaline phosphatase as above. 1 μg of the above adaptor and 0.1 μg of BamHI-digested pYJ38 were ligated using T4 ligase as described above. The modified vector was designated pYJ45. A 1.8 Kb SmaI fragment containing the modified AOX2 promoter was obtained by digesting 50 μg of pYJ45 with SmaI. The fragment was isolated from a 0.8% preparative agarose gel. 0.3 μg of the fragment and 0.3 μg of SmaI-digested pBPfl were ligated as above to create the vector pYJ46. A 0.3 Kb EcoRI fragment was deleted from the 5' end of the AOX2 segment in pYJ46 as follows. 10 μg of pYJ46 was digested with EcoRI and treated with alkaline phosphatase as described above. A separate 50 μg aliquot of pYJ46 was also digested with EcoRI and a 1.5 Kb fragment was isolated from a 0.8% preparative agarose gel. About 0.3 μg each of phosphatased pYJ46 and the isolated fragment were ligated and transformed into E. coli as described above. One plasmid which had the correct structure was isolated and designated pYJ55.

EXAMPLE VII

Development of Strain GS115 (pYJ55)

Pichia pastoris GS115, a histidine auxotroph (NRRL Y-15851; his4) was transformed with plasmid pYJ55 (Example VI) as described in Example II. Genomic DNAs from stable His+ strains were analyzed by Southern filter hybridization to determine the location of the plasmid. One transformant containing pYJ55 integrated at the HIS4 locus was designated GS115 (pYJ55).

EXAMPLE VIII

Comparison of the AOX1 and AOX2 Promoters

Regulation and expression of the AOX1 and AOX2 promoters has been compared by determining the β-galactosidase activity of strains GS115 (pSAOH5) and GS115 (pYJ55). 100 ml cultures of each strain were grown in YNB plus 1% glycerol medium for 24 hr. at 30° C., shifted to YNB medium without a carbon source for 24 hr at 30° C., then shifted to a YNB medium with 0.5% methanol for 50 hr at 30° C. Samples of each culture were removed at the following times: (1) after 24 hr in glycerol medium, (2) after 24 hr in no carbon medium, and (3) after 24 and 50 hr in methanol medium. Extracts were prepared and assayed for β-galactosidase activity as described below. The results of these assays are shown in Table 2.

β-GALACTOSIDASE ASSAY (1) Solution Required:

| Z-buffer: | | Final Concentration |
|---|---|---|
| Na₂HPO₄.7H₂O | 16.1 g | 0.06 M |
| NaH₂PO₄ | 5.5 g | 0.04 M |
| KCl | 0.75 g | 0.01 M |
| MgSO₄.7H₂O | 0.246 g | 0.001 M |
| 2-mercaptoethanol | 2.7 mL | 0.05 M | fill up to 1 L; pH should be 7

0-Nitrophenyl-β-D-galactoside (ONPG)

Dissolve 400 mg ONPG (Sigma N-1127) in 100 mL of distilled water to make a 4 mg/mL ONPG solution (2) Cell-free Protein Extract Preparation:

Each sample was washed once in dH₂O, once in lysis buffer, and resuspended in lysis buffer at a concentration of 150 $A_{600}$/ml. 0.5 g of glass beads were added to a 350 μl aliquot of sample, and the mixture was vortexed four times for 60 seconds each with 1 minute intervals on ice. The cell slurry was removed from the glass beads, and the suspension was centrifuged for 5 minutes in a microfuge. The supernatant was transferred to a polypropylene microfuge tube for assaying. The amount of total protein in each extract was determined by the Bradford assay method (Bio-Rad). BSA served as the protein standard.

(3) Assay Procedure:

1-50 μl of cell-free protein extract was added to 1 ml of Z buffer. The mixture was then vortexed and incubated for 5 minutes at 30° C. The reaction was initiated by the addition of 0.2 ml of ONPG (4 mg/ml). 0.5 ml of a 1M Na₂CO₃ solution was added to stop the reaction at an appropriate time ($A_{420}$<1). The absorbance at 420 nm was then read.

(4) Calculation of β-galactosidase Activity Units

1 U=1 nmole of orthonitrophenol (ONP) formed per minute at 30° C. and pH 7. 1 nmole of ONP has an absorbance at 420 nm ($A_{420}$) of 0.0045 with a 1 cm path length. Therefore, an absorbance of 1 at 420 nm represents 222 nmoles ONP/ml, or 378 nmoles ONP/1.7 ml (the total volume of supernatant being analyzed was 1.7 ml). Units expressed in Table 2 were calculated as follows:

$$U = \frac{A_{420}}{t \text{ (min)}} \times 378$$

That which is claimed is:

1. A recombinant DNA sequence encoding a methylotrophic yeast alcohol oxidase II regulatory region which is responsive to the presence of methanol as the sole carbon source for the host cell; and wherein said sequence is contained between the first EcoRI site from the 5' end and the start codon of the AOX2 structural gene as shown by the restriction map of FIG. 1(b).

2. A DNA sequence encoding a yeast alcohol oxidase II regulatory region wherein said DNA sequence is

```
                    -1490                    -1470
           TCCATCTTCTACGGGGGGATTATCTATGCTTTGACCTCTAT

-1450                    -1430                    -1410
     CTTGATTCTTTTATGATTCAAATCACTTTTACGTTATTTATTACTTACTGGTTATTTACT

-1390                    -1370                    -1350
     TAGCGCCTTTTCTGAAAAACATTTACTAAAAATCATACATCGGCACTCTCAAACACGACA

-1330                    -1310                    -1290
     GATTGTGATCAAGAAGCAGAGACAATCACCACTAAGGTTGCACATTTGAGCCAGTAGGCT

-1270                    -1250                    -1230
     CCTAATAGAGGTTCGATACTTATTTTGATAATACGACATATTGTCTTACCTCTGAATGTG

-1210                    -1190                    -1170
     TCAATACTCTCTCGTTCTTCGTCTCGTCAGCTAAAAATATAACACTTCGAGTAAGATACG

-1150                    -1130                    -1110
     CCCAATTGAAGGCTACGAGATACCAGACTATCACTAGTAGAACTTTGACATCTGCTAAAG

-1090                    -1070                    -1050
     CAGATCAAATATCCATTTATCCAGAATCAATTACCTTCCTTTAGCTTGTCGAAGGCATGA

-1030                    -1010                    -990
     AAAAGCTACATGAAAATCCCCATCCTTGAAGTTTTGTCAGCTTAAAGGACTCCATTTCCT

-970                     -950                    -930
     AAAATTTCAAGCAGTCCTCTCAACTAAATTTTTTTCCATTCCTCTGCACCCAGCCCTCTT

-910                     -890                    -870
     CATCAACCGTCCAGCCTTCTCAAAAGTCCAATGTAAGTAGCCTGCAAATTCAGGTTACAA

-850                     -830                    -810
     CCCCTCAATTTTCCATCCAAGGGCGATCCTTACAAAGTTAATATCGAACAGCAGAGACTA

-790                     -770                    -750
     AGCGAGTCATCATCACCACCCAACGATGGTGAAAAACTTTAAGCATAGATTGATGGAGGG

-730                     -710                    -690
     TGTATGGCACTTGGCGGCTGCATTAGAGTTTGAAACTATGGGGTAATACATCACATCCGG
```

-continued

```
      -670                      -650                      -630
AACTGATCCGACTCCGAGATCATATGCAAAGCACGTGATGTACCCCGTAAACTGCTCGGA

-610                      -590                      -570
TTATCGTTGCAATTCATCGTCTTAAACAGTACAAGAAACTTTATTCATGGGTCATTGGAC

-550                      -530                      -510
TCTGATGAGGGGCACATTTCCCCAATGATTTTTTGGGAAAGAAAGCCGTAAGAGGACAGT

-490                      -470                      -450
TAAGCGAAAGAGACAAGACAACGAACAGCAAAAGTGACAGCTGTCAGCTACCTAGTGGAC

-430                      -410                      -390
AGTTGGGAGTTTCCAATTGGTTGGTTTTGAATTTTTACCCATGTTGAGTTGTCCTTGCTT

-370                      -350                      -330
CTCCTTGCAAACAATGCAAGTTGATAAGACATCACCTTCCAAGATAGGCTATTTTTGTCG

-310                      -290                      -270
CATAAATTTTTGTCTCGGAGTGAAAACCCCTTTTATGTGAACAGATTACAGAAGCGTCCT

-250                      -230                      -210
ACCCTTCACCGGTTGAGATGGGGAGAAAATTAAGCGATGAGGAGACGATTATTGGTATAA

-190                      -170                      -150
AAGAAGCAACCAAAATCCCTTATTGTCCTTTTCTGATCAGCATCAAAGAATATTGTCTTA

-130                      -110                      -90
AAACGGGCTTTTAACTACATTGTTCTTACACATTGCAAACCTCTTCCTTCTATTTCGGAT

-70                       -50                       -30
CAACTGTATTGACTACATTGATCTTTTTTAACGAAGTTTACGACTTACTAAATCCCCACA

-10
AACAAATCAACTGAGAAAA
```

3. A DNA sequence as described in claim 1 wherein said sequence is operably linked to a heterologous gene.

4. A DNA sequence as described in claim 2 wherein said sequence is operably linked to a heterologous gene.

* * * * *